United States Patent [19]

Sharpless et al.

[11] Patent Number: 4,560,811

[45] Date of Patent: Dec. 24, 1985

[54] METAL-MEDIATED HALOHYDRIN FORMATION

[75] Inventors: Karl B. Sharpless, Brookline, Mass.; Roy A. Johnson, Kalamazoo, Mich.

[73] Assignee: Massachusetts Institute of Technology, Cambridge, Mass.

[21] Appl. No.: 571,961

[22] Filed: Jan. 18, 1984

[51] Int. Cl.[4] .................. C07C 29/64; C07C 31/20; C07C 31/34; C07C 33/40

[52] U.S. Cl. ....................... 568/848; 556/445; 560/231; 560/266; 568/649; 568/674; 568/676; 568/807; 568/811; 568/834; 568/845; 568/850

[58] Field of Search ............ 568/850, 848, 807, 811, 568/834, 845, 649, 674, 676; 560/231, 266; 556/445

[56] References Cited

U.S. PATENT DOCUMENTS

| | | | |
|---|---|---|---|
| 1,315,229 | 9/1919 | McElroy | 568/850 |
| 2,307,875 | 1/1943 | Buc et al. | 568/850 |
| 3,351,635 | 11/1967 | Kollar | 568/850 |
| 4,313,008 | 1/1982 | Jones | 568/676 |

OTHER PUBLICATIONS

K. Tani et al., *Tetrahedron Letters* (1979) 32:3017–3020.
S. Yamada et al, *J. Am. Chem. Soc.* (1977) 99:1988–1990.
R. Michaelson et al., *J. Am. Chem. Soc.* (1977) 99:1990–1992.
Katsuki and Sharpless, *J. Am. Chem. Soc.* (1980) 102:5974–5976.
Sharpless et al., *Pure and Appl. Chem.* (1983) 55:589–604.

*Primary Examiner*—J. E. Evans
*Attorney, Agent, or Firm*—Bertram I. Rowland

[57] ABSTRACT

Novel methods for making chlorohydrins are provided using a Lewis acid catalyst with an olefin and peroxy compound or where an enantiomer is desired, a Lewis acid catalyst in combination with a chiral alcohol, particularly glycol, and a combination of a peroxy compound and alkenol. In certain situations, an epoxide may be employed.

12 Claims, No Drawings

METAL-MEDIATED HALOHYDRIN FORMATION

BACKGROUND OF THE INVENTION

1. Field of the Invention

Synthetic organic chemistry is an essential adjunct in a wide variety of industrial fields. Synthesis is important to the preparation of drugs, monomers, additives for fuels, oils, plastics, and the like. In the field of drugs or other physiologically active compounds, it is frequently important to be able to make one of two stereoisomers. To prepare compounds it is usually necessary to functionalize a compound which is commercially available and is of substantially simpler structure than the final product. The oil and coal industries provide a large variety of olefins, which are hydrocarbons or mono-heterofunctionalized.

It is therefore of substantial economic interest to be able to functionalize, that is, enhance the value of various simple compounds, so that they can be used as intermediates in the preparation of more valuable compounds. Epoxides and halohydrins, the latter being useful as intermediates to epoxides, can be used in a wide variety of reactions to produce products of commercial importance.

2. Description of the Prior Art

Methods of asymmetric synthesis may be found in J. D. Morrison and H. S. Mosher, "Asymmetric Organic Reactions," Prentice-Hall, Englewood Cliffs, N.J., 1971, 258–262; S. Yamada et al., *J. Am. Chem. Soc.*, (1977) 99:1988; R. C. Michaelson et al., ibid., (1977) 99:1990; H. B. Kagan et al., *Angew. Chem. Int. Ed. Eng.*, (1979) 18:45; K. Tani et al., *Tetrahedron Lett.*, (1979) 3017; and H. Wynberg and B. Marsman, *J. Org. Chem.*, (1980) 45:158; and K. B. Sharpless and T. R. Verhoeven, *Aldrichimica Acta.*, (1979) 12:63. Tani et al., *Tetrahedron Lett.* (1979) 32:3017–3020 describe the use of molybdenum catalysts to asymmetrically epoxidize olefinic hydrocarbons in the presence of chiral diols. Katsuki and Sharpless, *J. Am. Chem. Soc.*, (1980) 102:5974–5976 report asymmetric epoxidation employing a combination of titanium alkoxide and tartrates. See also Mimoun, *J. Mol. Catal.*, (1980) 7:1–29; Sharpless et al., *Pure and Applied Chem.*, (1983) 55:589–604; and Sharpless et al., ibid., (1983) 55:1823–1836. Propylene oxide is opened non-selectively with $TiCl_2(OEt)_2$. Choukroun, *Inorg. Chem. Acta.* (1981) 58:121-2.

SUMMARY OF THE INVENTION

Improved methods are provided for producing halohydrins, particularly chlorohydrins, employing a heavy metal Lewis acid, where depending upon the substrate and additional materials, chiral or achiral products may be obtained. Hetero-substituted or unsubstituted olefin and a peroxy compound are employed in conjunction with the Lewis acid.

DESCRIPTION OF SPECIFIC EMBODIMENTS

The subject invention involves the use of a halo heavy metal Lewis acid, e.g. mixed halo-alkoxide heavy metal compound, by itself or in combination with a chiral glycol, for the production of halohydrins, particularly chlorohydrins, from an olefin and a peroxy compound. The reaction is carried out by combining the substrate and the Lewis acid in an inert organic medium at mild conditions, usually reduced temperatures, for a sufficient time for production of the halohydrin. The halohydrin may then be isolated and may be used in a variety of ways, including production of an epoxide in accordance with known ways.

Where a chiral halohydrin is desired, the reaction will be carried out in the presence of a chiral glycol, particularly a di-oxo-substituted chiral glycol and an alkenol is employed. In contrast to epoxidation employing a titanium tetraalkoxide and optically active tartrate for epoxidation of allylic alcohols with hydroperoxide, the opposite stereospecificity is obtained in this halohydrin yielding process.

In discussing the subject invention, the various components involved in the reaction will be described, followed by a description of the method, as well as setting forth any other components and conditions employed in the method.

Compositions

Halo Heavy Metal Reagent

The reagents employed in the subject invention involve heavy metal Lewis acid compounds having at least one halogen, wherein one or more of the halogens may be replaced by an alkoxide. The metal has a coordination of at least 4, usually 6, and will be a metal of Groups 4b to 6b of atomic number 22 to 74, particularly those metals of Group 4b to 5b of atomic number 22 to 73 of the Periodic Chart (Handbook of Chemistry and Physics, 44th ed., Chemical Rubber Publishing Company, pp. 448–449). The metals of interest include titanium, tantalum, zirconium and vanadium. Besides halo and oxy, vanadium will include an oxygen.

The preferred and by far most effective metal is titanium, which is clearly the metal of choice. The halogen will usually be chlorine. Other reactions may occur with the halogens other than chlorine and to that extent, the chloro group will normally be employed. Therefore the preferred catalyst is a chlorotitanium compound having 0 to 3 alkoxide groups. The alkoxides, when present, are conveniently lower alkoxides of from 1 to 6 carbon atoms, preferably of from 2 to 6 carbon atoms, more preferably branched alkoxides, having from 1 to 2 alpha-alkyl substituents of from 1 to 2 carbon atoms.

Illustrative catalysts include $TiCl_2(OiPr)_2$, $TiCl_4$, $TiCl(OMe)_3$, $TiBr(OiPr)_3$, $TiCl_2(OMe,O$-$t$-$But)_2$, $TiCl_3(OiPr)$, $TaCl_3(OiPr)$, $TiCl_2(Oneo$-$hex)_2$, $TiCl_2(Osec$-$but)_2$, $TiCl_3(Osec$-$pent)$, $TiCl_2(O$-$3$-$pent)_2$, $TiCl_2$·(Diethyl tartrate), $TiCl(OMe, OEt, OiPr)_3$, $TiCl_2$(mixture of OMe, OEt, OiPr)$_2$, (OiPr-isopropoxy, OMe-methoxy, Ot-but-tert.-butoxy, Oneo-hex-$\alpha,\alpha$-dimethyl-but-1-oxy, Osec-but-2-butoxy, Osec-pent-2-pentoxy, O-3-pent-3-pentoxy).

Where an asymmetric product is desired, a chiral glycol will be employed with the catalyst, usually a 1,2-di-oxo-substituted glycol, more particularly a 1,2-di-non-oxo-carbonyl-substituted glycol will be employed, e.g. tartrate, where the tartrate may be employed as the mono- or di-salt, -ester, -amide, or combinations thereof. The groups bonded to the non-oxo-carbonyl will generally be of from about 1 to 12 carbon atoms, more usually of from 1 to 10 carbon atoms, where substituents on the heteroatoms (oxygen and nitrogen) may be aliphatic, alicyclic, aromatic or heterocyclic, where the nitrogen may be an annular atom. Since the groups bonded to the non-oxo-carbonyl will affect the yields and enantiomeric efficiency, these groups may be varied based on the teachings of the examples to ensure enhanced results.

Of particular interest are reagents where a titanium alkoxy halide is combined with a tartrate at predetermined ratios. These compounds will for the most part have the following formula:

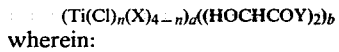

wherein:
X is alkoxide of from about 1 to 6 carbon atoms;
n is 1 to 4;
Y is alkoxy of from 1 to 12 carbon atoms, more usually of from 1 to 6 carbon atoms or amino, including mono- and di-substituted amino, of the formula —NZZ', where Z and Z' are the same or different, and are hydrogen, hydrocarbon of from 1 to 12 carbon atoms, or other non-interfering substituted hydrocarbon group, generally lacking an active heteroatom, such as hydroxyl, mercapto, basic amino, or the like, or Z and Z' may be taken to form a ring of from 5 to 7 annular members;
a is 1;
b will generally range on the average from about 0.4 to 2, more usually about 0.5 to 1.5.

Where the halo-metal reagent is used in combination with a chiral glycol, the two components of the reagent may be precombined prior to combining with the olefin substrate or may be combined in combination with the substrate.

Where one of the halogens of the metal halide is to be substituted by an alkoxide, this can be achieved in conventional ways. The metal halide may be combined with the alkoxide of an appropriate metal, e.g. alkali metal, for example, lithium or sodium, in an inert polar solvent in approximately stoichiometric ratio and the product separated from the inorganic salt. Alternatively the titanium halide and titanium tetraalkoxide may be mixed in appropriate proportions in an inert halohydrocarbon solvent with cooling in a dry atmosphere.

Substrate

The substrate employed in the subject invention is a heterosubstituted or unsubstituted olefin. The substrate will normally have at least 3 carbon atoms and usually not more than about 60 carbon atoms, more usually not more than about 30 carbon atoms. The carbon limitation is set forth as a matter of convenience and not necessity, since for the most part compounds of interest for organic synthesis will generally be relatively small compounds. However, in those instances where a compound greater than 60 carbon atoms may be of interest, the subject invention would be applicable, subject to certain considerations such as solubility, number of functionalities present and desired degree of reaction.

For the most part, there will be basically three categories of substrates: olefin; hydroxyolefin, usually allylic; and other heterosubstituted isolated olefins. Each of these compounds may be used for the formation of a halohydrin, although they will not be interchangeable, so far as obtaining a chiral product.

The substrates may be substituted with a wide variety of non-interfering heterosubstituents, that is substituents having heteroatoms, particularly non-metallic heteroatoms of Groups V to VI of the Periodic Chart and silicon. The substituents may involve such heteroatoms as oxygen, nitrogen, halogen, silicon, or the like. Illustrative substituents include fluoro, esters, amides, ethers, cyano, etc., where the esters and amides may have the carbonyl or oxy or amino proximal to the olefin. Whether a substituent interferes or does not interfere, may be determined empirically, since both the location and the nature of the atom to which the heteroatom is bonded will affect whether it is non-interfering. Desirably olefin substrates will not be in conjugation with a multiply bonded heterofunctionality.

Where a chiral epoxide is desired an alkenol will be employed, where the hydroxyl group will generally be from 1 to 2 carbon atoms from the closest olefinic carbon atom, preferably separated by one carbon atom, i.e. allylic. The hydroxy may be primary or secondary, normally primary. For a stereoisomeric epoxide, an unsymmetrical olefin is employed, that is, prochiral.

The olefin will usually be mono-, di-, or trisubstituted, preferably having at least one hydrogen atom bonded to an olefinic carbon atom, more preferably, having from 1 to 2 hydrogen atoms bonded to olefinic carbon atoms. The carbon bonded to hydroxy should also have at least one hydrogen atom. Where an isolated (not proximate or adjacent—1-2 carbon atoms—to a coordinating functionality, e.g., hydroxyl) olefin is employed, a mono- or disubstituted olefin is preferred.

The products of this invention can be used either directly or indirectly for the formation of a wide variety of physiologically interesting compounds. These compounds include steroids, lipids, prostaglandins, terpenoids, hormones, saccharides, CNS drugs, alpha- and beta-andrenergic blocking agents, antiarrythmic drugs, vasodilator drugs, analgesics, antibiotics, amino acids, and the like.

Peroxy Compounds

The peroxy compounds which are employed in the subject invention may be organic peroxides, e.g. hydroperoxides or disubstituted peroxides, generally of from 4 to 20 carbon atoms, more usually of from about 4 to 12 carbon atoms. Of particular interest are the tertiary alkyl hydroperoxides and peroxides, such as tert.-butyl hydroperoxide, di-tert.-butyl peroxide, di-neohexyl peroxide, neooctyl hydroperoxide, etc., although other tertiary peroxides or hydroperoxides may be used such as cumyl hydroperoxide, p-methoxycumyl hydroperoxide, 3,3,6,6-tetramethyl-1,2-dioxacyclohexane, 2,4-dimethylhex-3-in-2,4-dihydroperoxide, or the like. The hydroperoxide or peroxide should have acceptable thermal stability, so that the tertiary hydroperoxides or peroxides will be the ones of choice. However, the choice of peroxide or hydroperoxide will affect the yield and depending upon the particular reaction, one may be more favored than another. The peroxides will normally be used in conjunction with TiCl$_4$, while hydroperoxides may be used in conjunction with any of the reagents.

Method

As the reaction medium, inert solvents will be employed, particularly halohydrocarbon solvents and ethers. The solvents should be relatively free of reactive protons (particularly acidic), such as are present with alcohols, mercaptans and acids. The solvent should be substantially anhydrous, ensuring that substantially no water is present. The water will normally react with the catalyst, so as to hydrolyze the catalyst.

Mild conditions will normally be employed with temperatures below about 80° C., usually below about 30° C., and generally in the range of about −100° to 25° C., more usually in the range of about −50° to 25° C. Conveniently, the reaction is carried out in an inert dry atmosphere, such as nitrogen or argon.

The order of addition is not essential to obtaining a reaction, but may have a dramatic effect on the yield of reaction and purity of product. Specifically, where the glycol is not present, initial addition of the peroxide to the substrate, followed by addition of the Lewis acid reagent, is by far the preferred mode of addition, resulting in yields which are in some cases double those obtained when the order of addition is reversed.

The concentration of the various reactants may be varied widely, depending upon their solubility, the desired rate of reaction, ease of separation of the product from the other materials in the reaction mixture, viscosity and the like. Generally the concentration of the substrate will vary from about 0.001M to about 2M, more usually from about 0.005M to 1M.

The time for the reaction will vary widely, depending upon the various components of the reaction. Usually, the reaction time will be at least 5 minutes, and not more than 72 hours, more usually ranging from about 10 minutes to about 24 hours. The more active the Lewis acid reagent, the less the time required for reaction.

The ratio of halo metal reagent to substrate will vary. The reagent will usually be in at least about equimolar ratio to the substrate and generally not more than about a 3 molar ratio, more usually not more than about a 2 molar ratio, and preferably ranging from about 1.1 to 1.5 molar ratio to substrate. Usually, the peroxy compound will be present in at least about an equivalent ratio to the Lewis acid reagent and not more than about twice the reagent, usually not more than about 1.5 times the reagent. The chiral glycol will be present in a molar ratio of about 0.5 to 2, more usually about 0.5 to 1.5 to reagent. Depending upon the choice of glycol, one may obtain as the product one or the other of the diastereomers.

After completion of the reaction, the Lewis acid reagent is destroyed using a mildly acidic aqueous solution and, where the product is in the organic layer, the organic layer is dried and the product isolated. Where the product is in the aqueous layer, the product may be salted out of the aqueous layer and the aqueous layer extracted repeatedly, employing, for example, the same solvents as those employed for the reaction, or other polar solvents which have low water solubility in a salt solution.

Depending upon the choice of substrate, Lewis acid reagent and the presence or absence of the chiral glycol, the products will vary. With an allylic alcohol as substrate, in the absence of a chiral glycol, employing the haloalkoxytitanium catalyst and a peroxy compound, the product will be a mixture of $\alpha,\beta$-dihydroxy-$\gamma$-chloro- and $\alpha,\gamma$-dihydroxy-$\beta$-chloro products. In the presence of a chiral glycol, the product will be substantially the regioselective product $\alpha,\beta$-dihydroxy-$\gamma$-chloro, with opposite face selection to regioselective epoxidation. Better optical yields are obtained with the disubstituted olefins as compared to higher substituted olefins.

Finally, an olefin and a Lewis acid metal catalyst, e.g. $TiCl_4$, in the presence of a peroxy compound will give a halohydrin in high yield.

Instead of an olefin, an epoxide can be used for producing a chlorohydrin in high yield. To prepare the chlorohydrin, a hydroxymethyl epoxide is added to a combination of the Lewis acid reagent and the glycol. The conditions are analogous to those employed with the olefin and peroxy compound. Ring opening is achieved stereospecifically and regioselectively to produce the $\alpha,\beta$-dihydroxy-$\gamma$-chloro product.

The following examples are offered by way of illustration and not by way of limitation.

EXPERIMENTAL

*General Methods*—Melting points were obtained with a Thomas-Hoover melting point apparatus and are uncorrected. The $^1H$ NMR spectra were obtained with the Bruker 250 and 270 MHz instruments. All optical rotations were measured at 20.0° C. Brine refers to a saturated aqueous solution of sodium chloride. The structural formulas of the numbered compounds are provided at the end of the Experimental section.

*Dichlorodiisopropoxytitanium* (3)—Methylene chloride (11.8 ml) was placed in a dry, round bottomed flask which was protected from atmospheric moisture. To this was added under $N_2$ titanium tetraisopropoxide (6.0 ml, 5.72 g, 0.020 mole). The resulting solution was cooled in an ice bath. Titanium tetrachloride (2.2 ml, 3.8 g, 0.020 mole) was added over a period of one minute. The resulting solution was stored at room temperature under nitrogen. The solution was 2M in titanium.

*Chlorotriisopropoxytitanium* (4)—Methylene chloride (10 ml) was placed in a dry, round bottomed flask and was protected from atmospheric moisture. Under $N_2$, titanium tetraisopropoxide (9.0 ml, 8.58 g, 0.030 mole) was added to the solvent. The resulting solution was cooled in an ice bath and titanium tetrachloride (1.1 ml, 1.89 g, 0.010 mole) was added. The resulting solution is 2M in titanium and was stored at room temperature under $N_2$.

In the first series of experiments, two basic procedures were employed referred to as A and B.

A. Into dry $CH_2Cl_2$ (about 30 ml) is introduced 200 mg of either cis or trans-5-decene (1.42 mmole) under argon at a reduced temperature and tert.-butyl hydroperoxide (TBHP) added, followed by addition of the Lewis acid reagent. The time between the addition of TBHP and the Lewis acid reagent was about 3–5 min.

B. To a solution of the 5-decene and Lewis acid reagent (ratios as described above) at reduced temperature under argon, the TBHP was added.

For each reaction, the workup involved adding about 5–10 ml of aqueous saturated sodium sulfate and about 30 ml of diethyl ether. The aqueous phase was extracted with the diethyl ether and dried over magnesium or sodium sulfate. Chromatography was performed using ethyl acetate (~15%) in hexane.

The following Table 1 indicates the procedure employed, the Lewis acid reagents, the ratio of reactants, the reaction conditions, and the yield.

TABLE 1

| Lewis Acid+ Reagent | Equivalent Ratio TBHP*/Reagent | Procedure | Conditions T °C. | Time, hr | Yield, %** |
|---|---|---|---|---|---|
| TiCl(OiPr)$_3$ | 2.4/2 | B | −25 | 1 | 0.5–1.0 |
| | | | 25 | 4 | |
| TiCl$_2$(OiPr)$_2$ | 2.4/2 | B | −25 | 0.5 | 40 |
| | | | 0 | 30; or | |
| | | | −25 | 2 | |
| TiCl$_4$ | 2/1.2 | B | −78 | 0.5 | 86 |
| TaCl$_5$ | 1.2/1.2 | B | −78 | 2 | 16° |
| | | | 0 | 1 | |
| | | | 25 | 26 | |
| ZrCl$_4$ | 1.2/1.2 | B | −78 | 1 | 10° |
| | | | 0 | 0.25 | |

TABLE 1-continued

| Lewis Acid+ Reagent | Equivalent Ratio TBHP*/Reagent | Pro-cedure | Conditions T °C. | Time, hr | Yield, %** |
|---|---|---|---|---|---|
| VOCl$_3$ | 1.2/1.2 | A | −78 | 15 | 10° |

+OiPr - isopropoxide; TaCl$_5$ and ZrCl$_4$ were insoluble in CH$_2$Cl$_2$
*TBHP - tert.-butyl hydroperoxide
**Based on original substrate, amount of chlorohydrin obtained after chromatography
°The remainder is starting material which may be recovered and converted.

The chlorohydrin gives the corresponding epoxide upon treatment with potassium carbonate in dry methanol. The cis- and trans-epoxides are prepared by treating the corresponding chlorohydrins (threo and erythro respectively) with potassium carbonate in methanol. By a simple TLC, one can determine the stereoisomerism of the epoxides; employing 5% ethyl acetate in hexane, the trans-epoxide migrates more rapidly than the cis-epoxide.

In the next set of reactions, ethyl ether was used as the solvent. At −78° C., a solution of 5-decene (1.46 mmole) and TBHP (1.2 eq) was heated with TiCl$_4$ (1.2 eq). A brown precipitate appeared. After 15 min, the solution was warmed to room temperature and stirred for 20 min. The solution became yellow and the gum disappeared. The workup was as previously described, providing 73% yield of the anticipated chlorohydrin.

In the next reaction, di-t.-butyl peroxide was employed instead of TBHP. To 30 ml of CH$_2$Cl$_2$ containing trans-5-decene (about 1.5 mmole) and di-t.-butyl peroxide (1.2 eq) at 0°, TiCl$_4$ (1.2 eq) was added. The solution was stirred for 15 min and the reaction quenched with aqueous saturated sodium sulfate. The workup was as previously described and the yield was 59%.

When the reaction was repeated except that the reaction was carried out for 30 min at 0° C., and either 1.2 eq or 2.4 eq of trimethylsilyl chloride was present, the yields of the chlorohydrin were 77% and 70%, respectively.

Optimization of reaction conditions resulted in the following recommended procedure, illustrated for 1-methoxydec-2-ene as substrate. To a −78° solution of the substrate (0.1654 g, 0.92 mmole) in 20 ml CH$_2$Cl$_2$, under N$_2$, was added TBHP (1.2 eq.), followed by TiCl$_4$ (1.2 eq.). The reaction was worked up after 5 hr by pouring the cooled solution into Et$_2$O/sat. Na$_2$SO$_4$ and allowing to stir for 1 hr. Separation of layers and purification of the crude product by chromatography resulted in a 92% yield of 1-methoxy-2-hydroxy-3-chlorodecane, with the chlorohydrin in the threo configuration.

In general, the presence of TBHP in excess of 1.2 eq. has no beneficial effect and in many cases has a deleterious effect. The order of addition is important as described above, and dilute solutions (0.05M) are advantageous. The reaction time is not critical, but the reaction will in general be complete within 1 hr.

(2S,3S)-2-Hydroxymethyl-2,3-diphenyloxirane (9b)

A chromatographically and enantiomerically pure sample of 9b was prepared according to Katsuki and Sharpless, J. Am. Chem. Soc., (1980) 102:5974–5976; this product was purified by recrystallization from methylene chloride-hexane to give colorless needles, mp 88°–89° C.; [α]$_D$+80.9° (c, 2.39, EtOH).

3-Chloro-2,3-diphenylpropan-1,2-diol (8b)

A. (2S,3R)-8 from 9b

The procedure described for opening of 18 was followed, using TiCl$_2$(O-i-Pr)$_2$ (0.43 mmole), (+)-DET (0.48 mmole), and epoxide 9b (0.092 g, 0.0041 mole). Following chromatography (8 g, of silica gel, 15% EtOAc-hexane), crystalline 8b (0.052 g) was obtained; [α]$_D$−115° (c, 1.30, EtOH). Recrystallization from ethyl acetate-hexane gave colorless crystals, mp 108°–109° C.

B. (2R,3S)-8 from Chlorohydroxylation of cis-α-Phenylcinnamyl Alcohol 7

Methylene chloride (5 ml) containing TiCl$_2$(O-i-Pr)$_2$ (0.60 mmole) was cooled in a CCl$_4$-Dry Ice bath. (+)-DET (0.145 g, 0.70 mmole) in CH$_2$Cl$_2$ (1 ml) was added. After 5 minutes, allylic alcohol 7 (0.105 g, 0.50 mmole) was added and, finally, tert-butyl hydroperoxide (1.0 mmole) was added. The solution was stored at −20° C. overnight and then worked up by pouring into and stirring with sat'd aqueous Na$_2$SO$_4$ (0.5 ml) and ether (30 ml) for 60 minutes. The mixture was filtered through Celite, dried over MgSO$_4$, filtered, concentrated, and chromatographed over silica gel (5 g, 20% EtOAc-hexane). In this experiment the desired product (0.062 g) was recrystallized from methylene chloride-hexane giving 0.045 g of colorless crystals, mp 100°–107° C. $^1$H NMR spectrum was identical to that of (2S,3R)-8. The ee of this reaction and the effects of various changes in reaction conditions on the ee are summarized in Table 2.

TABLE 2

| Mole Ratio | | | | Tartaric Derivative | | e.e.* |
|---|---|---|---|---|---|---|
| Alcohol | Ti | Tartaric | Ti Complex | (HOCHCOY)$_2$Y = | Temp °C. | (2R, 3S) |
| 1 | 1.2 | 1.4 | TiCl$_2$(OiPr)$_2$ | (+) OEt | 0 | 30 |
| " | " | " | " | " | −20 | 28 |
| " | " | " | " | " | +24 | 25 |
| 1 | 1 | 0.5 | " | " | 0 | 32 |
| " | " | " | " | " | −20 | 20 |
| 1 | 1.2 | 1.4 | " | (+) NH$_2$ | 0 | 10 |
| " | " | " | " | (+) NHCH$_2$φ | 0 | 35 |
| " | " | " | TiCl(OiPr)$_3$ | (+) OEt | 0 | 17+ |
| " | " | " | TiCl$_{2.5}$(OiPr)$_{1.5}$ | " | 0 | 36 |
| 1 | 1.2 | 0.6 | TiCl$_2$(OiPr)$_2$ | (+) NHCH$_2$φ | 0 | 24 |
| " | " | " | TiCl(OiPr)$_3$ | " | 0 | 80 |

*enantiomeric efficiency
+2S,3R configuration

Chlorohydroxylation of trans-3-Phenyl-2-propen-1-ol (11, Cinnamyl Alcohol)

(2R,3S)-3-Chloro-3-phenylpropan-1,2-diol (13a) and 3-tert-Butylperoxy-3-phenylpropan-1,2-diol (14)

Dichlorodiisopropoxytitanium (3.0 ml of a 2M solution in $CH_2Cl_2$, 60 mmole) was added to methylene chloride (20 ml) in a dry round bottom flask (50 ml). The resulting solution was protected from moisture with a $CaCl_2$ drying tube and was stirred and cooled in an ice-water bath. A solution of (+)-diethyl tartrate ((+)-DET, 1.45 g, 70 mmole) in $CH_2Cl_2$ (4 ml) was added to the preceding solution. A pale brownish-yellow color developed. After 10 minutes, trans-3-phenyl-2-propen-1-ol (0.670 g, 50 mmole, Aldrich Chem. Co.) was added as a solid. The color of the solution changed to yellow. After 5 minutes, tertiary-butyl hydroperoxide (2.2 ml of a 4.6M solution) was added and the reaction solution was stirred at 0° C. The progress of the reaction was followed by TLC (40% ethyl acetate-hexane, 40% acetonehexane) using aliquots of the reaction quenched in sat'd aqueous sodium sulfate and ether. The reaction was worked up after 7 hours by pouring into ether (75 ml) and sat'd $Na_2SO_4$ (6 ml). The mixture was stirred 20 minutes, filtered through Celite, and the filtrate dried over $MgSO_4$. The dried solution was filtered, concentrated, and chromatographed over one Merck Size B Lobar silica gel column. The column was eluted with 6% acetone in methylene chloride and fractions of 11 ml volume were collected. Fractions 59–69 (0.194 g) were mixtures and were rechromatographed as described below. Fractions 70–110 contained (2R,3S)-3-chloro-3-phenylpropan-1,2-diol (13a) and were pooled, 0.474 g; $[\alpha]_D + 50.3°$ (c, 3.70, EtOH).

Fractions 59–69 from above were rechromatographed over a Merck Size B Lobar silica gel column using 30% ethyl acetate in hexane (75 fractions) and 40% ethyl acetate-hexane for elution. Ten milliliter fractions were collected. Fractions 90–96 contained a less polar material, 0.024 g (0.107 mmole, 2%), characterized by the NMR spectrum as 3-tert.-butylperoxy-3-phenylpropan-1,2-diol (14). Fractions 97–100 were mixed and fractions 100–128 contained additional 13a, 0.124 g (total 13a was 0.598 g, 0.322 mole, 64%).

Reaction of Cinnamyl Alcohol (11) with $TiCl_2(OiPr)_2$/TBHP

As a control reaction, the reaction of cinnamyl alcohol (0.134 g, 1.0 mmole) with $TiCl_2(OiPr)_2$ (0.0012 mole) was carried out as described above except that (+)-DET was omitted from the reaction. The reaction was carried out at 0° C. and was complete in less than 40 minutes. TLC (40% ETOAc-hexane; 30% acetone-hexane) revealed a product less polar than starting material and several products more polar than starting material. These were partially separated by chromatography (silica gel, 10 g, 20% acetone-hexane) into three components: less polar, 0.005 g, NMR similar to that of a mixture of 2,3-dichloro-3-phenylpropylmethyl ethers; a mixture of intermediate polarity, 0.028 g, NMR suggestive of a mixture of 3-t-butylperoxy-3-phenylpropan-1,2-diol and 3-i-propoxy-3-phenylpropan-1,2-diol in a ratio of 15:4; and a more polar, major component, 0.082 g (0.44 mmole, 44%) whose NMR spectrum is consistent with a mixture of 3-chloro-3-phenylpropan-1,2-diol (13) and 2-chloro-3phenylpropan-1,2-diol in a ratio of 7:3.

(2R,3R)-2,3-Epoxy-3-phenylpropan-1-ol (18a) from 13a

A solution of 13a (0.155 g, 0.833 mmole) in ether (10 ml) was stirred with brine (10 ml) and sodium hydroxide (4 pellets). The reaction was complete within 40 minutes as detected by TLC (60% ethyl acetate-hexane). Additional ether was added, the layers were separated, and the organic layer was washed with brine. After drying ($MgSO_4$), the ether layer was filtered, concentrated, and chromatographed over silica gel (5 g) packed as a slurry in 35% ethyl acetate-hexane (5 ml fractions). (2R,3R)-2,3-Epoxy-3-phenylpropan-1-ol (18a, 0.100 g, 0.667 mmole, 80%) was obtained in fractions 5–9; $[\alpha]_D + 33.7°$ (c, 3.09, EtOH). The NMR spectrum is identical with the spectrum of an authentic sample of 18b. The authentic sample of 18b is reported to be of 95% optical purity and has $[\alpha]_D + 55.8°$ (c, 2.00, EtOH); the enantiomeric excess of 18a, and therefore of 13a, prepared above is 60% as determined by comparison of optical rotations.

Using (−)-α-methoxy-α-trifluoromethylphenylacetyl chloride, the Mosher ester of 18a (0.030 g) was prepared. The crude reaction product was chromatographed over silica gel (4 g) packed as a slurry in 10% ethyl acetate-hexane. Fractions of 4.5 ml volume were collected. The pure ester (0.059 g) was collected in fractions 4–7. Although $^1H$ NMR signals are seen for each diastereomer, their separation is not sufficient to allow accurate integration of each. The ratio of the two diastereomers are qualitatively consistent with the ee observed by optical rotation.

Opening of 2,3-Epoxy-3-phenylpropan-1-ol(18) with Di-chlorodiisopropoxytitanium (3)

A. Opening of (2R,3R)-18 with 3 and (+)-DET

A solution of $TiCl_2(O-i-Pr)_2$ (0.30 ml of a 2M solution in $CH_2Cl_2$, 0.60 mmole) in $CH_2Cl_2$ (5 ml) was protected from atmospheric moisture, stirred, and cooled in an ice-water bath. (+)-Diethyl tartrate (0.145 g, 7.0 mmole) in $CH_2Cl_2$ (1 ml) was added to the solution. After 10 minutes, (2R,3R)-2,3-epoxy-3-phenylpropan-1-ol (0.075 g, 0.50 mmole, $[\alpha]_D + 55.8°$) was added to the solution. The reaction was complete within 15 minutes as determined by TLC (50% ethyl acetate-hexane) of a sample quenched in aq. sodium sulfate and ether. The reaction was worked up by stirring with aq. sat'd $Na_2SO_4$ (1 ml) and ether (35 ml), filtering through Celite, and drying over $MgSO_4$. The crude product was chromatographed over silica gel (5 g) packed as a slurry in 6% acetonemethylene chloride (5 ml fractions). Fractions 10–20 were pooled, 0.070 g (0.376 mmole, 75%), and contained (2R,3S)-3-chloro-3-phenylpropan-1,2-diol (13a); $[\alpha]_D + 84.5°$ (c, 3.15, EtOH); NMR spectrum identical to that of the sample of 13a.

B. Opening of (2R,3R)-18 with 3 and (−)-DET

Under the same conditions as described in Part A above, except that (−)-DET was used in place of (+)-DET, a sample of (2R,3R)-18 was converted into (2R,3S)-13; $[\alpha]_D + 86.3°$ (c, 3.31, EtOH).

C. Opening of (2R,3R)-18b with 3 and no DET

Using the conditions described in Part A above, except that the DET was omitted, a sample (2R,3R)-18 (0.075 g) was converted to a mixture of (2R,3S)- 13 and the 2-chloro-1,3-diol 37 (0.051 g), $[\alpha]_D - 44.5°$ (c, 2.56, EtOH).

D. Opening of (2S,3S)-18b with 3 and (+)-DET

Using the conditions described in Part A above, except that (2S,3S)-18 (0.075 g, $[\alpha]_D-55.8°$) was used in place of (2R,3R)-18, there was obtained (2S,3R)- 13 (0.056 g); $[\alpha]_D-81.7°$ (c, 2.64, EtOH).

E. Opening of (2S,3S)-18b with 3 and (−)-DET

Using the conditions described in Part A above, except that (2S,3S)-18 was substituted for (2R,3R)-18, and (−)-DET was substituted for (+)-DET, there was obtained (2S,3R)- 13 (0.065 g); $[\alpha]_D-69.8°$ (c, 2.65, EtOH).

F. Opening of (2S,3S)-18b with 3 and no DET

Using the conditions described in Part A above, except that (2S,3S)-18b was substituted for (2R,3R)-18 and the DET was omitted, there was obtained a mixture of (2S,3R)-13 and 37 (0.048 g); $[\alpha]_D+37.5°$ (c, 1.92, EtOH).

Chlorohydroxylation of trans-3-(4'-chlorophenyl)-2-propen-1-ol (12)

(2R,3S)-3-Chloro-3-(4'-chlorophenyl)propan-1,2-diol (15a) and 3-tert-butylperoxy-3-(4'-chlorophenyl)propan-1,2-diol (16)

Dichlorodiisopropoxytitanium (1.8 ml of a 2M solution in $CH_2Cl_2$, 3.6 mmole) was added to methylene chloride (20 ml) in a dry, round-bottom flask. The solution was protected from atmospheric moisture, stirred, and cooled in an ice-water bath. A solution of (+)-diethyl tartrate (0.87 g, 4.2 mmole) in $CH_2Cl_2$ (2 ml) was added to the preceding and a pale brownish-yellow color formed. After 15 minutes, trans-3-(4'-chlorophenyl)-2-propen-1-ol (12, 0.505 g, 3.0 mmole) was added as a solid. The reaction solution became yellow in color. tert-Butyl hydroperoxide (1.32 ml of a 4.6M solution in $CH_2Cl_2$) was added and the reaction was maintained at ice-water temperature. The progress of the reaction was followed by TLC (60% ethyl acetate-hexane) of samples quenched in aq. $Na_2SO_4$-ether. Only a trace of starting 12 remained after 3.67 hr and the reaction was worked up after 4 hours by stirring with sat'd aq. $Na_2SO_4$ (4 ml) and ether, filtering through Celite, and drying over $MgSO_4$. The crude product was chromatographed over one Merck Size B Lobar silica gel column using 5% acetone-methylene chloride for elution. The first 100 fractions were 6 ml in volume; thereafter the volume was increased to 10 ml and the solvent changed to 10% acetone-methylene chloride. Diethyl tartrate eluted in fractions 45-85. Fractions 118-124 contained two components and were rechromatographed as described below. Fractions 125-140 contained (2R,3S)-3-chloro-3-(4'-chlorophenyl)propan-1,2-diol (15a, 0.369 g) which crystallized $[\alpha]_D+40.0°$ (c, 2.59, EtOH).

Rechromatography of fractions 118-124 from above over one Merck Size A Lobar silica gel column in 30% ethyl acetate-hexane (5 ml fractions) gave pure 3-tert-butylperoxy-3-(4'-chlorophenyl)propan-1,2-diol (16), 0.007 g (0.03 mmole, 1%) in fractions 22 and 23. Fractions 24 and 25 were mixed. Fractions 26-60 contained additional 15a (0.102 g, total 0.471 g, 2.14 mmole, 71%).

A small sample of 15a was acetylated with acetic anhydride and 4-dimethylaminopyridine in pyridine. The reaction product consisted of a single component when analyzed by TLC.

(2S,3R)-3-Chloro-3(4'-chlorophenyl)propan-1,2-diol (15b)

Using the conditions described above for the preparation of 15a, except substituting (−)-DET for (+)-DET, a sample of 12 (0.168 g, 1.0 mmole) was treated with $TiCl_2(O$-$i$-$Pr)_2$ (1.2 mmole), (−)-DET (1.4 mmole), and TBHP (2 mmole). Following work-up, the crude reaction product was chromatographed over silica gel (8 g) packed as a slurry in 5% acetone-methylene chloride (5 ml fractions). Fractions 11-15 were mixtures and were not further separated. Fractions 16-27 (0.080 g) were (2S,3R)-3-chloro-3-(4'-chlorophenyl)propan-1,2-diol (15b); $[\alpha]_D-38.6°$ (c, 3.40, EtOH); NMR ($CDCl_3$) was identical to that of the (2R,3S)-15a.

(2R,3R)-2,3-Epoxy-3-(4'-chlorophenyl)propan-1-ol (19a)

A solution of 15a (0.112 g, 0.51 mmole) in ether (10 ml) was gently stirred with brine (10 ml) and sodium hydroxide (3 pellets). The reaction was complete after 7.5 hours as determined by TLC (60% ethyl acetate-hexane) and was worked-up by adding more ether, separating the layers, and washing the ether layer with brine. The ether was dried ($MgSO_4$), filtered, and concentrated. The viscous, residual oil (0.080 g, 0.435 mmole, 87%) crystallized; $[\alpha]_D+29.8°$ (c, 2.22, EtOH), reported for 95% optically pure 19a, $[\alpha]_D+44.1°$. Recrystallization of 0.072 g from ether-hexane gave colorless crystals (0.062 g) of (2R,3R)-2,3-epoxy-3-(4'-chlorophenyl)propan-1-ol (19a), mp 59°-68° C.; $[\alpha]_D+31.2°$ (c, 2.30, EtOH).

Using (−)-α-methoxy-α-trifluoromethylphenylacetyl chloride, the Mosher ester of 19a (0.023 g) was prepared. The crude reaction product was chromatographed over silica gel (4 g) packed and eluted with 10% ethyl acetate-hexane. Fractions of 4 ml volume were collected and the product (0.040 g) was found in fractions 4-7. The enantiomer excess calculated from the optical rotation is 68%. The NMR data is qualitatively consistent with this value.

Chlorohydroxylation of p-Methoxycinnamyl Alcohol (20)

A solution of $TiCl_2(O$-$i$-$Pr)_2$ (1.2 mmole) in $CH_2Cl_2$ (6 ml) was stirred and cooled to 0° C. (+)-DET (0.290 g, 1.4 mmole) in $CH_2Cl_2$ (1 ml) was added. After 10 min, p-methoxycinnamyl alcohol (0.164 g, 1.0 mmole) was added and 7 min later, TBHP (2 mmole) was added. The resulting solution was kept at 0° to −5° C. for 20 hr and then worked up. During TLC examination of the reaction in progress, it was seen that as the quenched aliquots of the reaction stood (in sat'd. aq. $Na_2SO_4$-ether made acidic by hydrolysis of the titanium complex), the major reaction product was changed to a considerably more polar compound. The TLC also indicated formation of several by-products in the reactions. During workup the reaction was quenched as usual in sat'd. aq. $Na_2SO_4$ (1 ml) and ether (40 ml), but was stirred at RT for 6 hr and left in contact overnight. The clear organic layer was decanted and the oily aqueous phase was washed with ether. The combined ether phases were dried ($MgSO_4$), etc., and the crude product chromatographed over silica gel (10 g, ethyl acetate, 6 ml fractions). The main product (0.061 g) was obtained in fractions 13-24 and from the NMR spectrum appeared to be a 4:1 mixture of 1,2,3-trihydroxy-3-(p-methoxyphenyl)-propanes (21) that are epimeric at C-3.

2-Methylenehexadecan-1-ol (22)

A solution of diisobutylaluminum hydride in $CH_2Cl_2$ (47 ml of a 1M solution, 0.047 mole, Aldrich Chem. Co.) was stirred under nitrogen in a round-bottom flask and cooled in an ice-water bath. To this was added dropwise over a period of 4 minutes a solution of 2-methylenehexadecanoic acid, methyl ester (2.82 g, 20 mmole) in $CH_2Cl_2$ (20 ml). The reaction was complete within 30 minutes as determined by TLC (20% ethyl acetate-hexane) of a sample quenched in brine-ether. The reaction was worked up after one hour by diluting with methylene chloride (300 ml) and adding several milliliters each of methanol and water. A gelatinous mass formed which broke up upon vigorous swirling. The mixture was filtered through Celite and the filtrate dried over $MgSO_4$. Following filtration and concentration, an oily residue was obtained. The residue crystallized and was recrystallized by dissolving in hexane at room temperature then cooling in the freezer. Crystals were collected from the cold hexane by rapid filtration. 2-Methylenehexadecan-1-ol (22) was obtained in a first crop (1.718 g) of colorless crystals, mp 33°–34° C., and a second crop (0.081 g, total 1.799 g, 0.0071 mole, 71%).

Chlorohydroxylation of 2-Methylenehexadecan-1-ol (22)

2-Chloromethylhexadecan-1,2-diol (23a)

A. Standard Conditions

A stirred solution of dichlorodiisopropoxytitanium (0.30 ml of a 2M solution in $CH_2Cl_2$, 0.60 mmole) was protected from moisture with a drying tube. To this was added a solution of (+)-diethyl tartrate (0.145 g, 0.70 mole) in $CH_2Cl_2$ (1 ml). The resulting pale brownish yellow solution was cooled in an ice-water bath and after 10 minutes, 2-methylenehexadecan-1-ol (0.127 g, 0.50 mmole) was added as the solid. After 7 minutes, a solution of tert-butyl hydroperoxide (0.22 ml of a 4.6M solution in $CH_2Cl_2$, 1.0 mmole) was added and the solution maintained at ice-water temperature. The progress of the reaction was followed by TLC (30% ethyl acetatehexane) of samples quenched in aq. $Na_2SO_4$-ether and was essentially complete after 4 hours. The reaction product mixture was chromatographed over silica gel (6 g) packed as a slurry in and eluted with 30% ethyl acetate-hexane. Fractions of 5.5 ml volume were collected. Fraction 3 (0.021 g) contained the desired product together with traces of less polar materials. Fractions 4–6 (0.097 g, total 0.118 g, 0.38 mmole, 76%) contained 2-chloromethylhexadecan-1,2-diol (23a), which was an oil at room temperature but became crystalline below room temperature; $[\alpha]_D$ 0.000° (c, 1.00, EtOH).

Using the above conditions, except as indicated below, the following results were obtained.

TABLE 3

| | EE Optimization Experiments with 2-Methylenehexadecan-1-ol | | | | |
|---|---|---|---|---|---|
| Entry | Alcohol/Ti/Tartr. (ratio) | Ligand | TBHP | Temp., °C. | ee |
| 1 | 1/1.2/1.4 | (+)-DET | 2 | 0 | 73% |
| 2 | 1/1.2/1.4 | " | " | 0 | 68 |
| 3 | 1/1.2/0.6 | " | " | 0 | 68 |
| 4 | 1/1.2/1.4 | (+)-DIPT* | " | 0 | 62 |
| 5 | 1/1.2/1.4 | " | " | −20 | 58 |
| 6 | 1/2.4/1.2 | " | " | 0 | 63 |

*DIPT — diisopropyltartrate

1-Chlorohexadecan-2-one (25)

Periodic acid (excess) was added to a solution of 2-chloromethylhexadecan-1,2-diol (23a, 0.021 g, 0.068 mmole) in wet ether (15 ml). The progress of the reaction was followed by TLC (30% ethyl acetate-hexane) and within 70 minutes, the diol 23a was completely transformed to a new, nonpolar product. Additional ether (15 ml) was added and the organic solution was washed with water (2×) and brine. The ether layer was dried ($MgSO_4$), filtered, and concentrated, leaving 0.017 g (0.062 mmole, 91%) of a crystalline material. Recrystallization from methanol gave 0.009 g of 1-chlorohexadecan-2-one (25), mp. 52.5°–53.5° C. (lit.[16] mp., 52°–52.5° C.).

d,l-2-Hydroxymethyl-2-tetradecyloxirane (26)

A solution of 2-methylenehexadecan-1-ol (22, 0.254 g, 1.0 mmole) and m-chloroperbenzoic acid (Aldrich 80% purity, 0.225 g, 1.05 mmole) was stirred at 25° C. for 2 hours. The solution was then extracted with aq. $NaHCO_3$, with brine, and then dried over $Na_2SO_4$. The solution was filtered, concentrated, and the crude product was chromatographed over silica gel (5 g) packed as a slurry in 15% ethyl acetate-hexane. The column was eluted with the same solvent system and 5 ml fractions were collected. Fraction 5 (0.070 g) contained desired product and a trace of a less polar impurity and was crystalline. Fractions 6–9 (0.166 g, total 0.236 g, 0.875 mmole, 87%) were pure crystalline product. Recrystallization from cold hexane gave colorless crystals of d,l-2-hydroxymethyl-2-tetradecyloxirane (26); mp 37°–38.5° C.

(2S)-2-Hydroxymethyl-2-tetradecyloxirane (26b)

A solution of Ti(O-t-Bu)$_4$ (0.34 ml, 1.0 mmole) and (+)-DET (0.248 g, 1.2 mmole) in $CH_2Cl_2$ (10 ml) was prepared at room temperature. The solution was cooled to −20° C. in a $CCl_4$-Dry Ice bath and 2-methylenehexade-can-1-ol (22, 0.254 g, 1.0 mmole) was added. The mixture was allowed to warm slightly until the alcohol 22 completely dissolved after which the solution was cooled to −20° C. again. A solution of TBHP in toluene (0.6 ml of a 3.34M solution, 2.0 mmole) was added. The solution was stirred at −20° C. and after 2 hr TLC (30% acetonehexane, 30% EtOAc-hexane) showed some 22 remaining. The reaction was quenched after 4 hr by stirring with saturated aqueous $Na_2SO_4$ (1 ml) and ether (80 ml) for 35 min, filtering through Celite, and drying over $MgSO_4$. TLC now showed a main product, a minor product, several trace products and a trace of unreacted starting material. Chromatography, (11.5 g silica gel, 8% acetonehexane, 6 ml fractions) gave the desired major product (26b) in fractions 8–12, 0.140 g (0.518 mmole, 51%). $^1H$ NMR identical to that of d,l-26.

Opening of d,l-2-Hydroxymethyl-2-tetradecyloxirane (26) with HCl, d,l,-2-Chloromethylhexadecane-1,2-diol (23) and 2-Chloro-2-hydroxymethylhexadecan-1-ol (27)

The epoxide 26 (0.030 g, 0.11 mmole) was dissolved in a saturated solution (15 ml) of HCl gas in $CH_2CL_2$. The epoxide was converted to two new products in less than 10 minutes (TLC on silica gel, 40% EtOAc-hexane). The solution was washed with aqueous 5% $NaHCO_3$ solution and dried over $Na_2SO_4$. The crude product was chromatographed (5 g silica gel, 15% EtOAc-hexane, 5 ml fractions) with the less polar product (0.009 g) eluted in fractions 14–19. The NMR spectrum of this compound was identical to that of 23a. Fractions 20 and 21 were mixtures.

The more polar component was eluted in fractions 22–32 and, after recrystallization from $CH_2Cl_2$-hexane, was a colorless, crystalline compound (0.010 g) having an NMR spectrum identical to that of 27.

Opening of 2-Hydroxymethyl-2-tetradecyloxirane (26) with Dichlorodiisopropyltitanium and (+)-DET A. Opening of d,l-26, d,l-2-Chloromethylhexadecan-1,2-diol (23)

A solution of dichlorodiisopropoxytitanium (0.30 ml of a 2M solution in $CH_2Cl_2$, 0.60 mmole) in $CH_2Cl_2$ (5 ml) was prepared in a dry flask and was protected from atmospheric moisture. (+)-Diethyl tartrate (0.145 g, 0.70 mmole) in $CH_2Cl_2$ (0.5 ml) was added and the resulting pale brownish-yellow solution was stirred and cooled in an ice-water bath. Solid d,l-2-hydroxymethyl-2-tetradecyloxirane (26) (0.135 g, 0.50 mole) was added. TLC (50% ethyl acetate-hexane) after 15 minutes showed the reaction to be complete. The reaction was stirred with sat'd aq. $Na_2SO_4$ (0.5 ml) and ether (30 ml) at room temperature for 30 minutes. The organic phase was filtered through Celite, dried ($MgSO_4$), filtered, and concentrated. The reaction product was chromatographed over silica gel (6 g; 20% ethyl acetate-hexane; 4 ml fractions). Fractions 5 and 6 contained product plus a trace of a less polar impurity. Fractions 7–11 (0.126 g, 0.412 mole, 82%) were d,l-2-chloromethylhexadecan-1,2-diol (23); $^1$H NMR was identical to that of 23a.

B. Opening of (2S)-26, (2S)-2-Chloromethylhexadecan-1,2-diol (23b)

Using the procedure described in Section A above, (2S)-26 (0.090 g, 0.33 mmole) was converted to the chlorodiol. The crude product was chromatographed over silica gel using 15% EtOAc-hexane and gave 0.065 g (0.248 mmole, 75%) of (2S)-23b.

2-Chloromethylhexadecan-1,2-diol, 1-Acetate (24a)

A. From 23a Produced by $TiCl_2(O-i-Pr)_2$/(+)-DET/TBHP

A solution of 23a (0.031 g) in pyridine (1 ml) with acetic anhydride (3 drops) and several small crystals of 4-dimethylaminopyridine was left at room temperature for 5 hours. TLC (30% ethyl acetate-hexane) showed one new less polar spot. The mixture was worked up by adding a few drops of water and, after 15 minutes, pouring into cold aqueous hydrochloric acid. The aqueous mixture was extracted with ether (3×), the combined ether extracts were washed with aq. $NaHCO_3$ and then dried over $MgSO_4$. After filtration and concentration, the crude product (0.030 g) was chromatographed over silica gel (5 g) packed as a slurry in 10% ethyl acetate-hexane. The column was eluted with the same solvent and fractions of 5 ml volume were collected. A less polar material (presumed to be a trace of diacetate) was eluted in fractions 2–4. The desired 2-chloromethylhexadecan-1,2-diol, 1-acetate (24a) was eluted in fractions 7–11, 0.026 g; $[\alpha]_D + 1.76°$ (c, 2.61, EtOH). When tris[3-(heptafluoropropylhydroxymethylene)-d-camphorato] europium (III) was added to the NMR sample, the spectrum was shifted. From the integrations for a major and a minor acetate methyl signal, the enantiomeric excess of the predominant enantiomer was determined to be 73%.

B. From d,l-23

Using the same procedure described, d,l-23 (0.045 g) was converted to d,l-monoacetate (0.035 g). The NMR spectrum of this compound is identical to the spectrum of 24a. When the europium shift reagent was added to the NMR sample, the spectrum shifted and signals for the two acetate methyl groups were seen. These results confirm the determination of enantiomeric excess described above.

C. From (2S)-23 Obtained from Opening (2S)-Epoxide 26b

Using the procedure described above, (2S)-23 (0.070 g) was converted to monoacetate 24b (0.066 g after chromatography over silica gel in 10% EtOAc-hexane); $[\alpha]_D - 1.95°$ (c = 1.64). From the NMR shift data, the ee is >95%.

The following Table 4 summarizes some of the results obtained with the opening of the epoxides 18 and 26.

TABLE 4

| | Epoxide Opening Reactions. | | | |
|---|---|---|---|---|
| Entry | Epoxy Alcohol | Reagent* | Chlorodiol(s) | $[\alpha]_D$ |
| 1 | (−)-18b | TiCP/(+)-DET | 13b | −81.7° |
| 2 | " | TiCP/(−)-DET | 13b | −69.8° |
| 3 | " | TiCP | 13b + 37 | +37.5° |
| 4 | (+)-18a | TiCP/(+)-DET | 13a | +84.5° |
| 5 | " | TiCP/(−)-DET | 13a | +86.3° |
| 6 | " | TiCP | 13a + 37 | −44.5° |
| 7 | (+)-26 | TiCP/(+)-DET | 23 | — |
| 8 | " | $HCl/CH_2Cl_2$ | 23 + 27 | — |

*TiCP = $TiCl_2(OiPr)_2$

Chlorohydroxylation of Geraniol (2R,3S)-3-Chloro-3,7-dimethyl-6-octen-1,2-diol (29a) and 3-tert-Butylperoxy-3,7-dimethyl-6-octen-1,2-diol (32).

Dichlorodiisopropoxytitanium [0.60 ml of a 2M solution (see note at the end of this experimental section) in $CH_2Cl_2$, 0.0012 mole] was added to $CH_2Cl_2$ (5 ml) in a dry round bottom flask. The solution was protected from atmospheric moisture and (+)-diethyl tartrate (0.290 g, 1.4 mmole) in $CH_2Cl_2$ (1 ml) was added. The resulting pale brownish-yellow solution was cooled in an ice-water bath and after 10 minutes geraniol (0.173 ml, 0.154 g, 1.0 mole) was added. After 5 minutes tert.-butyl hydroperoxide (0.44 ml of a 4.6M solution in $CH_2Cl_2$, 0.002 mole) was added. The progress of the reaction was followed by TLC (40% ethyl acetate-hexane) of aliquots quenched in aq. $Na_2SO_4$ and ether. The reaction was complete within 60 minutes (see note below) and was then stirred with sat'd aq. $Na_2SO_4$ (1 ml) and ether (30 ml) for one hour. The organic phase was filtered through Celite, dried (MgSO$_4$), filtered, and concentrated. Isolation of the major product and the most predominant of several minor products required repeated column chromatography. The columns run are indicated as Column A, B, C, D and E. Column A (7 g, silica gel, 30% ethyl acetate-hexane, 7 ml fractions) was ineffective and all fractions containing products were pooled and rechromatographed. Column B (7 g, silica gel, 10% acetone-hexane, 5 ml fractions) gave a mixture containing the minor product in fractions 8 and 9 (to column C), a mixture in fractions 10 and 11 (to column D), pure major product in fractions 12–16 (0.082 g), and a mixture of the major product and a very minor product in fractions 17–21 (8 mg). The major product was assigned the structure (2R,3S)-3-chloro-3,7-dimethyl-6-octen-1,2-diol (29a) and had [α]$_D$+4.36° (c, 2.64, EtOH).

Column C (5 g silica gel, 25% acetone-hexane, 3 ml fractions) was used to rechromatograph fractions 8 and 9 from above. Fraction 6 contained pure minor product. Fractions 7–9 were mixtures (to column D).

Column D (5 g silica gel, 10% acetone-hexane, 2.5 ml fractions) was used for rechromatography of fractions 10 and 11 of column B and fractions 7–9 of column C. Pure minor product was obtained in fractions 13–15 (pooled with fraction 6 of column C, total weight 0.010 g, 0.048 mmole, 5%), a mixture was obtained in fractions 16 and 17 that contained a third very minor product, fractions 18–24 were mixtures, and fractions 25–34 (0.013 g) contained major product.

Finally, fractions 18–24 of column D were rechromatographed over Column E (5 g silica gel, 30% ethyl acetate-hexane, 2.5 ml fractions) and additional major product 29a (0.019 g, total from columns B, D, and E 0.114 g, 0.55 mmole, 55%) was obtained in fractions 13–18.

Note—The dichlorodiisopropoxytitanium solution used in this experiment may have been more concentrated as a consequence of solvent evaporation. When this reaction was repeated using the same ratios of reagents except that a freshly prepared solution of dichlorodiisopropoxytitanium was used, the reaction required more than four hours to reach completion. When the reaction was again repeated with twice the amount of TiCl$_2$(O-i-Pr), (+)-DET, and TBHP, the reaction was nearly complete after 65 minutes.

(2R,3S)-3-Chloro-3,7-dimethyl-6-octen-1,2-diol, Diacetate (30)

A sample of 29a (0.041 g) was dissolved in pyridine (1.5 ml) and acetylated with acetic anhydride (6 drops) in the presence of 4-dimethylaminopyridine (small crystal). After 2 hours, TLC indicated that the reaction was complete. The reaction was quenched with water, cold aqueous hydrochloric acid was added and the mixture was extracted with ether. The ether was washed with aq. NaHCO$_3$ and with brine, then dried over MgSO$_4$. The crude reaction product was chromatographed (5 g of silica gel, 10% ethyl acetate-hexane, 5 ml fractions) and the desired product was obtained in fractions 4–6 (0.031 g).

(2S,3S)-2,3-Epoxygeraniol (31b)

A. From Ti(O-i-Pr)$_4$/(+)-DET in a Ratio of 1:1.1

The procedure of Katsuki and Sharpless was followed, using Ti(O-i-Pr) (0.57 g, 2.0 mmole), (+)-DET (0.45 g, 2.2 mmole), geraniol (0.308 g, 2.0 mmole), and TBHP (4 mmole of a 3.3M solution in toluene) in CH$_2$Cl$_2$ (10 ml) at −20° C. for 18 hr. The crude product was chromatographed over silica gel (12 g, 10% acetone-hexane, 7 ml fractions), giving 0.181 g of product in fractions 11–15 which contained two minor impurities (by TLC in 50% EtOH-hexane; 10% acetone-CH$_2$Cl$_2$). Rechromatography over silica gel (11 g, 5% acetone-CH$_2$Cl$_2$, 6 ml fractions) gave pure 31b (0.126 g) in fractions 10–14; [α]$_D$−4.0° (CHCl$_3$, c=2.29).

Acetylation of 31b (0.065 g) gave, after column chromatography (silica gel, 8% EtOAc-hexane, the acetate (0.049 g). The spectrum was shifted by the addition of tris[3-heptafluoropropylhydroxymethylene)-d-camphorato]europium (III) and from the integration of the signal for the methyl at C-3, the enantiomeric excess of the sample was estimated to be at least 92%. Addition of d,l-acetate to the sample confirmed that the shifted spectrum had been assigned correctly.

B. From Ti-(O-i-Pr)$_4$/(+)-DET in a Ratio of 1:0.5.

The experiment was identical to the above (Section A) with the exception that only 0.211 g (1.02 mmole) of (+)-DET was used. As above the product was obtained after two column chromatographs. Pure 31b (0.056 g) was obtained in fractions 12–14 of the second column but earlier fractions appeared to be contaminated with a tartrate ester (blue-green color when treated with phosphomolybdic acid). The pure 31b had [α]$_D$−3.2° (CHCl$_3$, C=2.19).

Acetylation of the pure fractions of 31b (0.034 g) gave, after column chromatography, the acetate (0.013 g); $^1$H NMR (D$_6$D$_6$) was identical to that of the above sample. When shifted with tris[3-(heptafluoropropylhydroxymethylene)-d-camphorato]europium (III), the acetate was found to have an enantiomeric excess of 70%.

Opening of (2S,3S)-2,3-Epoxygeraniol with Dichlorodiisopropoxytitanium and (+)-Diethyl Tartrate (2S,3R)-3-Chloro-3,7-dimethyl-6-octen-1,2-diol (29b)

Dichlorodiisopropoxytitanium (0.30 ml of a 2M solution in CH$_2$Cl$_2$, 0.60 mmole) was added to CH$_2$Cl$_2$ (5 ml) and protected from atmospheric moisture. (+)-Diethyl tartrate (0.145 g, 0.70 mole) was added and the resulting solution (light brownish-yellow) was cooled in an ice-water bath. (2S,3S)-2,3-Epoxygeraniol (0.085 g, 0.50 mole, [α]$_D$−4.1° (c, 1.77, CHCl$_3$), 92% ee) in CH$_2$Cl$_2$ (0.5 ml) was added to the reaction solution. The reaction was complete within 10 minutes as detected by TLC and was worked up by stirring with sat'd aq. Na$_2$SO$_4$ (0.5 ml) and ether (30 ml) for 30 minutes. The organic phase was filtered through Celite, dried (MgSO$_4$), filtered, and concentrated. The reaction product was chromatographed (6 g silica gel, 10% acetone-hexane, 4 ml fractions) and the product 29b obtained pure in fractions 15–18 (0.042 g). Fractions 9–14 and 19–20 contained desired product plus small quantities of minor products. The pure sample of 29b had [α]$_D$−15.6° (cm 1.43, EtOH) and its $^1$H NMR spectrum was identical to that of compound 29a. Since starting epoxide was 92% optical purity, 100% optically pure chloro-diol (29b) should have a rotation of −17°.

(2R,3R)-2,3-Epoxygeraniol (31a) from Chlorodiol 29a (2R,3S)-3-Chloro-3,7-dimethyl-6-octen-1,2-diol (0.032 g) was dissolved in reagent grade tetrahydrofuran (2 ml). Water (2 ml) and sodium hydroxide (⅛ pellet)

were added. The resulting two layered system was swirled occasionally. Conversion to a new product having the same $R_f$ as authentic 2,3-epoxygeraniol was complete within 15 minutes as detected by TLC (50% ethyl acetate-hexane). Brine (20 ml) was added to the mixture and this was extracted 2× with ether. The ether extract was dried (MgSO$_4$), filtered, and concentrated. The crude product (0.024 g) had several very minor impurities and so was chromatographed over silica gel (5 g) with 30% ethyl acetate-hexane. The desired product was in fractions 7-10, $[\alpha]_D+1.4°$ (c, 1.26, CHCl$_3$). $^1$H NMR was identical to that of the authentic sample of (2S,3S)-2,3-epoxygeraniol. The enantiomeric excess of this sample is 32% when the rotation is compared to that obtained for material of 92% optical purity.

(2S,3S)-3-n-Heptyl-2-hydroxymethyloxirane (35)

A. From Ti(O-i-Pr)$_4$/(+)-DET in a Ratio of 1:1.1

A solution of Ti(O-i-Pr)$_4$ (0.6 ml, 0.57g, 2.0 mmole) and (+)-DET (0.45 g, 2.2 mmole) in CH$_2$Cl$_2$ (10 ml) was cooled to −20° C. in a CCl$_4$-Dry Ice bath. trans-1-Decen-1-ol (0.312 g, 2.0 mmole) in CH$_2$Cl$_2$ (1 ml) was added followed by addition of TBHP (4.0 mmole in toluene). The resulting solution was stirred at −20° C. for 2.25 hr and then was quenched by stirring with sat'd aq. Na$_2$SO$_4$ (2 ml) and ether (80 ml) for one hour. The mixture was filtered through Celite, dried (MgSO$_4$), filtered, and concentrated. The crude product was chromatographed over silica gel (11.5 g, 10% acetone-hexane, 6 ml fractions) giving 0.244 g of 35 (1.42 mmole, 71%) which contained traces of a more polar impurity and a less polar impurity. This material was crystalline.

Chlorohydroxylation of trans-2-Decen-1-ol (33)

(2R,3S)-3-Chlorodecan-1,2-diol (34a)

A solution of TiCl$_2$(O-i-Pr)$_2$ (1.2 ml of a 2M solution, 2.4 mmole) in CH$_2$Cl$_2$ (5 ml) was stirred, cooled in an ice-water bath, and (+)-DET (0.58 g, 2.8 mmole) in CH$_2$Cl$_2$ (1 ml) was added. After 12 min, a solution of 33 (0.156 g, 1.0 mmole) in CHCl$_3$ was added. After 5 min. TBHP (2.7 mmole) in toluene was added and the solution was stirred 6 hr at ice bath temperature and then kept at −5° C. in the refrigerator for 80 hr. The reaction was quenched by stirring with sat'd aq. Na$_2$SO$_4$ (1 ml) and ether (35 ml) for 1 hr. The mixture was filtered through Celite, dried (MgSO$_4$), concentrated, and chromatographed. Several flash columns chromatographing over silica gel (in sequence, 20% acetone-hexane, 25% EtOAc-hexane, and 10% acetone —CH$_2$Cl$_2$) were required in order to obtain the desired product, 0.058 g containing a trace of a less polar compound and 0.032 g (total 0.090 g, 0.43 mmole, 43%) of pure compound (34a). The latter was used for optical rotation which was: $[\alpha]_D-24.2°$ (c=3.20, EtOH).

(2S,3R)-3-Chlorodecan-1,2-diol (34b) from Opening of (2S,3S)-3-n-Heptyl-2-hydroxymethyloxirane (35)

A solution of TiCl$_2$(O-i-Pr)$_2$ (0.43 mmole) and (+)-DET (0.10 g, 0.48 mmole) in CH$_2$Cl$_2$ (5 ml) was prepared at 0° C. (ice-water bath). (2S,3S)-3-n-Heptyl-2-hydroxymethyloxirane (35, 0.075 g, 0.43 mmole, from the 0.244 g sample of 35 described in Section A) was added as the solid. The reaction was complete within 45 min and was quenched by stirring with sat'd aq. Na$_2$SO$_4$ (1 ml) and ether (35 ml). The ether layer was decanted and dried (MgSO$_4$). The crude product was chromatographed over silica gel (9 g, 15% acetone-hexane) and the desired product was obtained in fractions 8-12. However, TLC in 15% acetone-CH$_2$Cl$_2$ showed a minor impurity in fractions 8 and 9. The combined fractions 8-12 were rechromatographed over silica gel (6 g, 7.5% acetone-hexane, 4 ml fractions). Fraction 9 was a mixture and fractions 10-13 were pure 34b (0.047 g), $[\alpha]_D+33.2°$ (c=1.58, EtOH); $^1$H NMR spectrum was identical to that of 34a.

Chlorohydroxylation of Linalool (39)

Using the same conditions described for the chlorohydroxylation of geraniol, linalool (39) was completely converted to a mixture of at least 2 major products and three minor products. These products were detected by TLC (40% ethyl acetate-hexane) but were not isolated.

Chlorohydroxylation of (+)-2-Methyl-1-hepten-3-ol (38)

A solution of 3 (1.2 mmole) in CH$_2$Cl$_2$ (6 ml) was cooled to 0° C. Added successively were (+)-DET (0.290 g, 1.4 mmole), 38 (0.128 g, 1.0 mmole), and TBHP (2 mmole). The reaction was stirred at 0° C. for 7 hours during which TLC showed the slow formation of two more polar components. The reaction was stirred overnight at room temperature after which starting material was completely consumed. The reaction was worked up in the usual manner and the product mixture chromatographed over silica gel (10 g, 8% acetone-hexane, 5.5 ml fractions). Fractions 7-9 contained the new, slightly more polar product (0.020 g, 0.12 mmole, 12%) which was assigned the tentative structure of 2-chloromethyl-1-hepten-3-ol (40) on the basis of its NMR spectrum.

Fractions 11-20 contained a mixture of two compounds (0.098 g, 0.54 mmole, 54%) in a ratio of 4:1 which are assigned the structure of the diastereomeric 1-chloro-2-methylheptan-2,3-diols (41) on the basis of the NMR spectrum of the mixture.

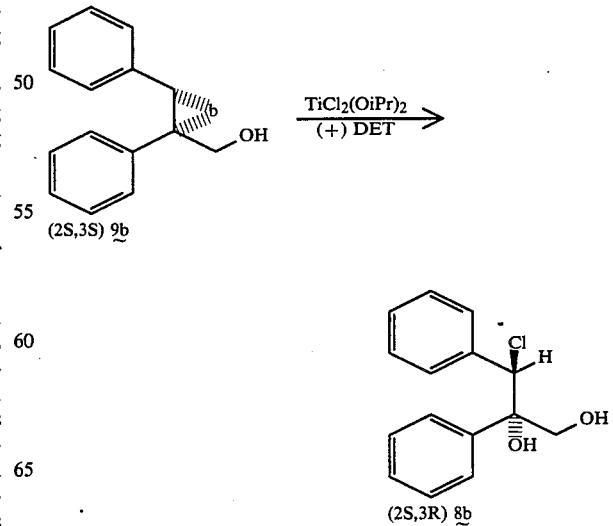

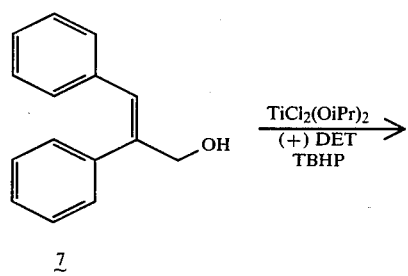
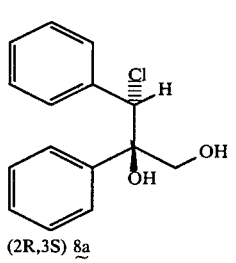
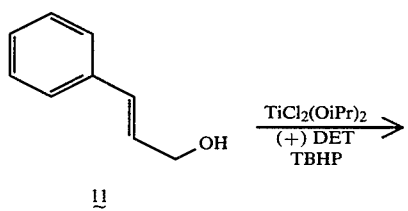
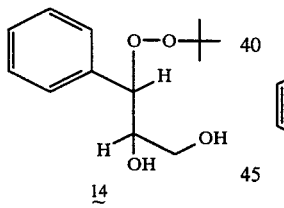
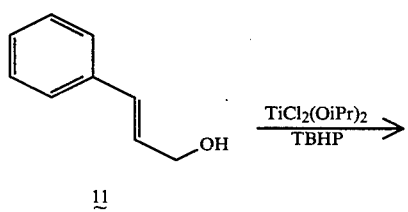
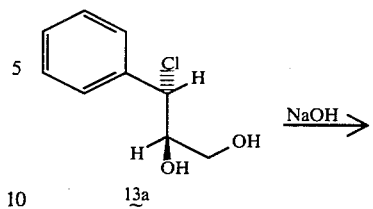
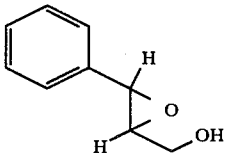
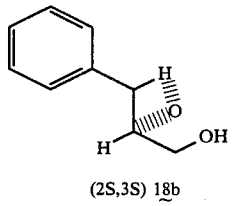
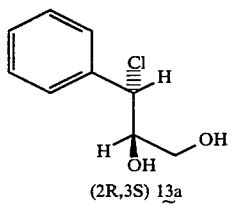

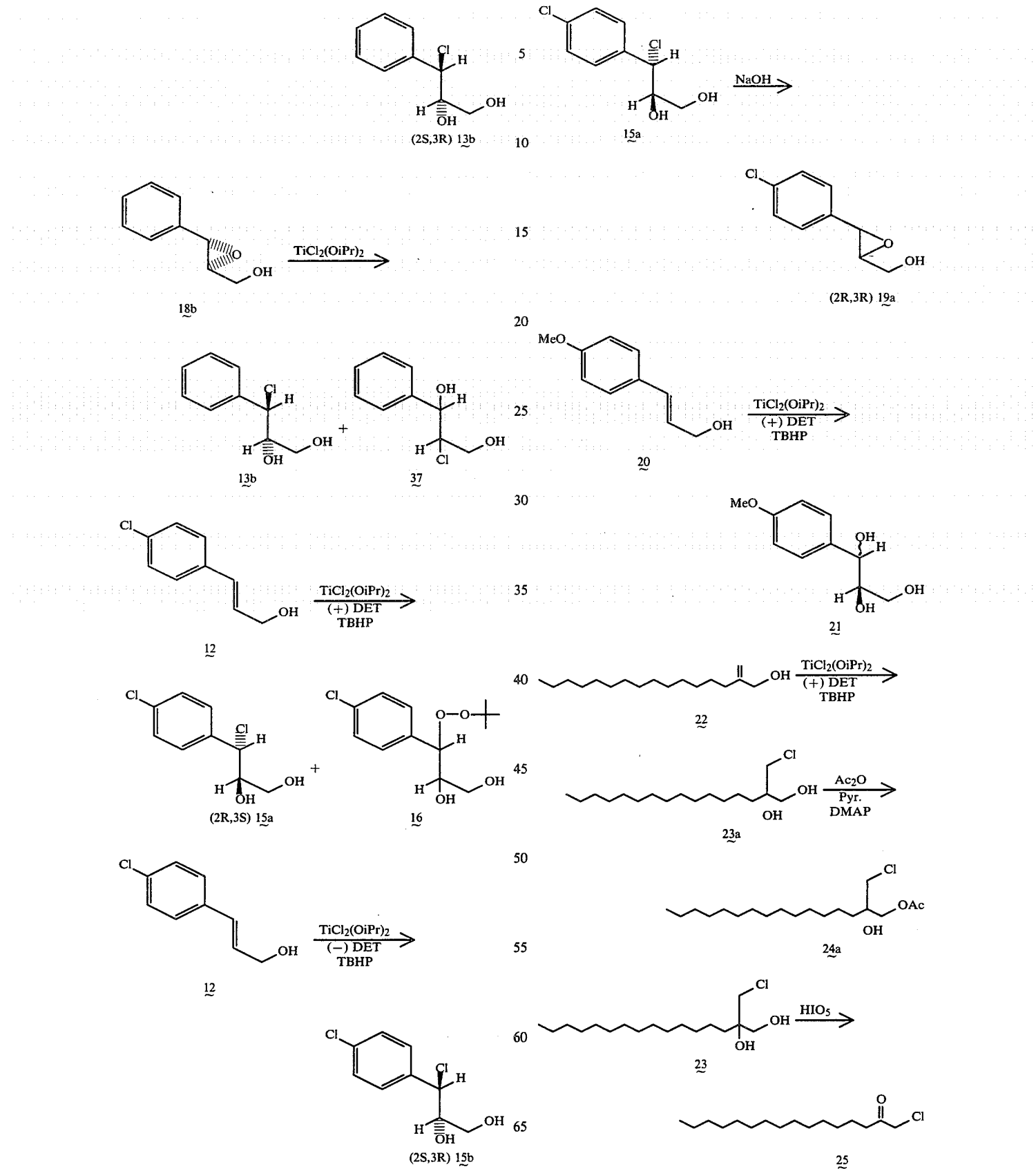

25
-continued
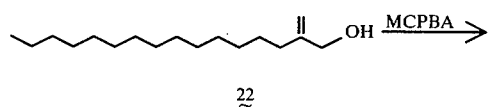
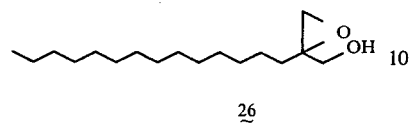
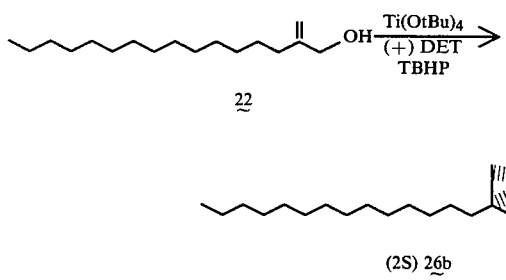
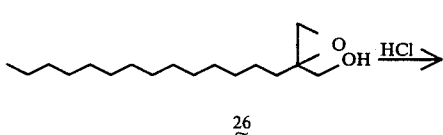
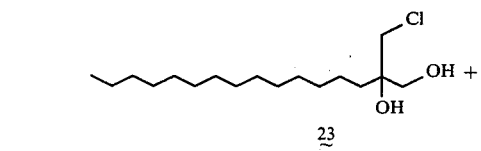
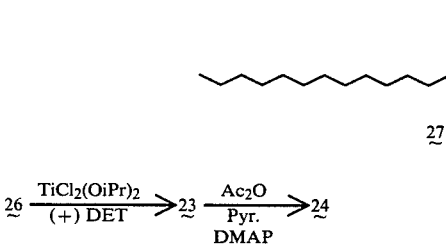
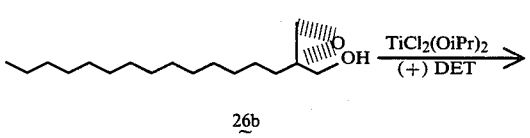
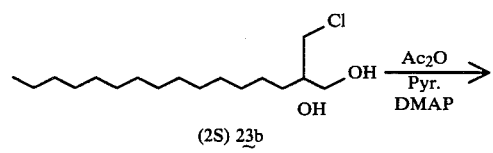
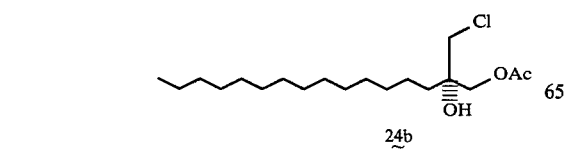
26
-continued
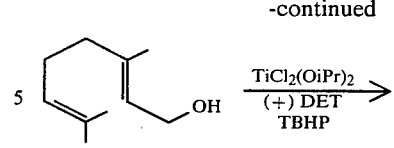
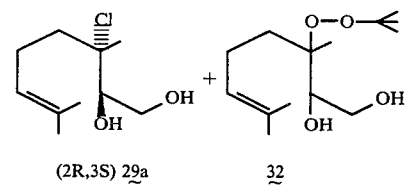
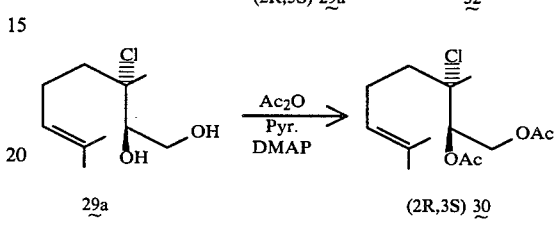
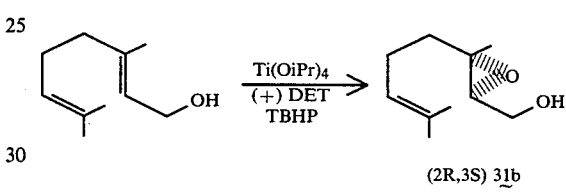
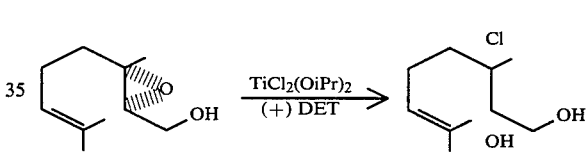
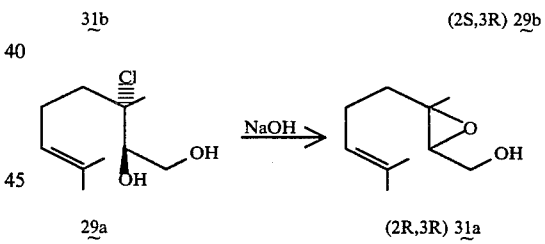
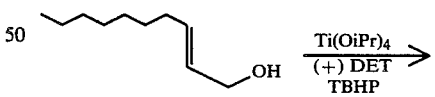
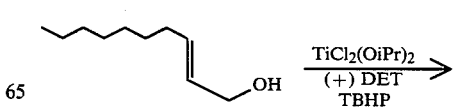

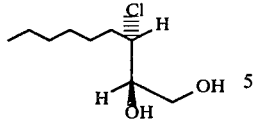

(2R,3S) 34a

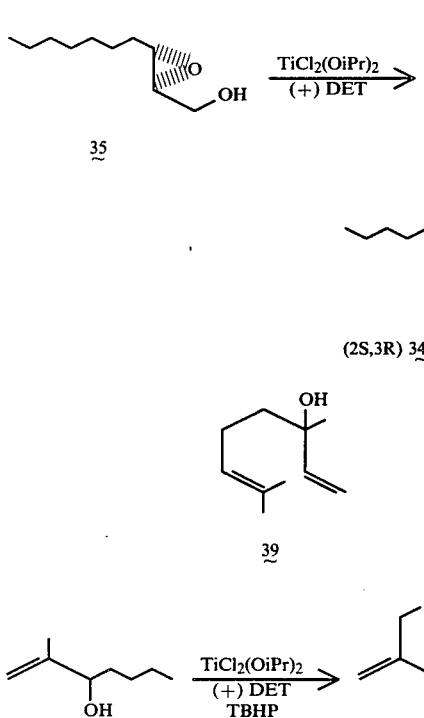

(2S,3R) 34b

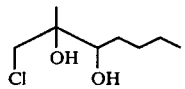

41

A number of reactions were carried out with a variety of heterosubstituted and unsubstituted olefins, also involving endocyclic olefins. The following is an exemplary procedure.

TYPICAL EXPERIMENTAL

A flame-dried 50 ml round-bottomed flask under $N_2$ is charged with the olefin and $CH_2Cl_2$ (distilled from $CaH_2$) to produce a 0.05M solution. This is cooled to $-78°$ and TBHP (1.2 eq., generally as a toluene solution) is added via syringe, followed by $TiCl_4$ (1.2 eq., $CH_2Cl_2$ solution). The reaction is monitored by tlc (EtOAc:Hexane). Favorable reactions are generally complete within one hour (often much sooner). If tlc shows much starting material remaining after 1 hr., additional $TiCl_4$ (1.2 eq.) is added. The reaction is worked up by pouring the cold mixture into $Et_2O$-sat. $Na_2SO_4$, and allowing it to stir at room temperature for one hour. The layers are separated and the ethereal layer is washed with sat. $Na_2SO_4$ and sat. NaCl, dried over $MgSO_4$ and evaporated on a rotary evaporator. The residual oil is purified by flash chromatography (EtOAc:hexane mixtures).

The following table indicates a number of compounds, specific conditions employed and the results. In most cases, no effort was made to optimize the yields.

TABLE 5

| | | Mole Ratio to Substrate | | | | Product | |
|---|---|---|---|---|---|---|---|
| | Substrate | $TiCl_4$ | TBHP | Time/hr. | Yield % | —OH | —Cl |
| a. | 4-t.-butylcyclohexene | 1.2 | 2.0 | 4 | 32 | 2 | 1 |
| b. | " | 1.2 | 1.2 | 3.5 | 95 | 2 | 1 |
| c. | 1-decene | 1.2 | 2.0 | 2 | 61 | | |
| d. | 1-methoxydec-2-ene | 1.2 | 1.2 | 5 | 92 | 2 | 3 |
| e. | 3,7-dimethyl-1-methoxy-oct-2,6-diene | 1.0 | 1.0 | 2 | 20 | 2 | 3,7 |
| f. | 2-hydroxy-6-methyl-hept-5-ene | 1.2 | 1.2 | 2.25 | 49 / 18 | — / 5 | 6 / 6 |
| g. | 2-acetoxy-6-methyl-hept-5-ene | 1.2 | 1.2 | 0.67 | 75 / 13 | — / 5 | 6 / 6 |
| h. | methyl cyclohex-3-enyl-1- i. formate ii. | 1.2 / 1.2 | 1.2 / 1.2 | 2 / 1° | 54 / 91 | 3 / 3 | 4 / 4 |
| i. | cyclohex-3-en-1-yl-formic acid | 1.2+ / 1.2 | 1.2 | 3 | 74* | 3 | 4 |
| j. | sodium cyclohex-3-en-1-yl-formate | 1.2+ / 1.2 | 1.2 | 2.5 | 78* | 3 | 4 |
| k. | trimethylsilyl cyclohex-3-en-1-ylformate | 1.2+ / 1.2 | 1.2 | 4 | 76* | 3 | 4 |
| l. | 2-acetoxy-6-methylhept-5-ene | 1.2 | 1.2+ | 2 | 60 | 5 | 6 |

+di-t.-butyl peroxide
°−20° C.
*as ester

The cyclic olefins provide mixtures of geometric isomers, the ratios depending upon the other substituent. The ratios are obtained from gas chromatography. The following table indicates the results.

| Example | cis:trans* | equatorial:axial+ |
|---|---|---|
| h.ii | 81:19 | 60:40 |
| i. | 82:18 | 27:73 |
| j. | 75:25 | 22:78 |

-continued

| Example | cis:trans* | equatorial:axial+ |
|---------|------------|-------------------|
| k. | 84:13 | 22:75 |

*relates to relationship of hydroxyl to carboxy, regardless of whether hydroxyl is in the 3- or 4- position.
+indicates whether all substituents can be in the equatorial position or the 3-substituent must assume an axial position.

The subject invention provides for the production of chlorohydrins from a variety of olefinic substrates, using a heavy metal, particularly titanium halide reagent. The use of the titanium reagent to prepare halohydrins from olefins provides high yields and frequently products different from other methods. With alkenols, the yields and enantiomeric efficiencies are high, where the reactions are carried out in the presence of an optically active glycol. Also, using a combination of a titanium reagent and an optically active glycol for the opening of epoxides can provide synthetic advantages in particular situations.

Although the foregoing invention has been described in some detail by way of illustration and example for purposes of clarity of understanding, it will be obvious that certain changes and modifications may be practiced within the scope of the appended claims.

What is claimed is:

1. A method for preparing a halohydrin, employing as reactant an olefin and peroxide, said method comprising:
combining said reactant with a heavy metal halide reagent under mild conditions in an inert medium for sufficient time to produce said halohydrin.

2. A method according to claim 1, wherein said heavy metal halide catalyst is a tetravalent chlorotitanium compound having from 0 to 3 alkoxide groups.

3. A method for preparing a chlorohydrin, employing as reactants a combination of olefin and organic peroxide, said method comprising:
combining said reactants with at least about an equimolar amount of a tetravalent chlorotitanium reagent having from 0 to 3 alkoxide groups under mild conditions in an inert organic medium for a sufficient time to produce said chlorohydrin.

4. A method according to claim 3, wherein said reactant has an hydroxymethyl substituent on said olefin and an optically active tartaric acid derivative is included in said reaction medium in an amount equal to at least 0.5 moles per atom of titanium, and wherein said olefin is prochiral, and the resulting chlorohydrin is optically active.

5. A method according to claim 4, wherein said tartaric acid derivative is an ester.

6. A method according to claim 4, wherein said tartaric acid derivative is an amide.

7. A method according to claim 3, wherein said alkoxide is isopropoxide.

8. A method according to claim 3, wherein said reagent is $TiCl_4$.

9. A method according to claim 3, wherein said reagent is titanium dichloride dialkoxide.

10. A method for preparing a chlorohydrin employing as reactants a combination of an olefin and an alkyl hydroperoxide,
said method comprising:
combining said reactants with at least about an equimolar amount of a tetravalent chlorotitanium alkoxide reagent under mild conditions in an inert organic medium for a sufficient time to produce said chlorohydrin.

11. A method according to claim 10, wherein said olefin is a prochiral allylic alcohol and tartaric acid or derivative thereof is combined with said reagent.

12. A method for preparing a chlorohydrin employing as reactants a heterosubstituted olefin and an alkyl hydroperoxide or dialkyl peroxide,
said method comprising:
combining said reactants with at least about an equimolar amount of $TiCl_4$ under mild conditions in an inert organic medium for a sufficient time to produce said chlorohydrin.

* * * * *